United States Patent
Nidorf

(10) Patent No.: US 10,206,891 B2
(45) Date of Patent: *Feb. 19, 2019

(54) METHOD OF TREATING CARDIOVASCULAR EVENTS USING COLCHICINE CONCURRENTLY WITH AN ANTIPLATELET AGENT

(71) Applicant: Murray and Poole Enterprises Limited, Gibraltar (GB)

(72) Inventor: Mark Nidorf, Menora (AU)

(73) Assignee: MURRAY AND POOLE ENTERPRISES LTD, Gibraltar (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/663,148

(22) Filed: Jul. 28, 2017

(65) Prior Publication Data
US 2017/0326083 A1   Nov. 16, 2017

Related U.S. Application Data

(63) Continuation of application No. 14/603,049, filed on Jan. 22, 2015, now Pat. No. 9,744,144, which is a continuation-in-part of application No. PCT/AU2013/001261, filed on Nov. 1, 2013.

(30) Foreign Application Priority Data

Nov. 2, 2012 (AU) .............................. 2012/904828
Nov. 5, 2012 (AU) .............................. 2012/904868

(51) Int. Cl.
| A61K 31/165 | (2006.01) |
| A61K 45/06 | (2006.01) |
| A61K 31/616 | (2006.01) |
| A61K 31/37 | (2006.01) |
| A61K 31/4365 | (2006.01) |

(52) U.S. Cl.
CPC ............ *A61K 31/165* (2013.01); *A61K 31/37* (2013.01); *A61K 31/4365* (2013.01); *A61K 31/616* (2013.01); *A61K 45/06* (2013.01)

(58) Field of Classification Search
None
See application file for complete search history.

(56) References Cited

U.S. PATENT DOCUMENTS

| 3,173,876 | A | 3/1965 | Zobrist |
| 3,276,586 | A | 10/1966 | Rosaen |
| 3,541,005 | A | 11/1970 | Strathmann et al. |
| 3,541,006 | A | 11/1970 | Bixler et al. |
| 3,546,142 | A | 12/1970 | Michaels et al. |
| 4,285,987 | A | 8/1981 | Ayer et al. |
| 8,415,395 | B1 | 4/2013 | Davis et al. |
| 2002/0015735 | A1 | 2/2002 | Hedden |
| 2006/0171948 | A1 | 8/2006 | Weinstein et al. |
| 2006/0286108 | A1 | 12/2006 | Bell |
| 2008/0039408 | A1 | 2/2008 | Freudenberger |
| 2009/0093548 | A1 | 4/2009 | Davis et al. |
| 2009/0170952 | A1 | 7/2009 | Davis |
| 2009/0299155 | A1 | 12/2009 | Yang |
| 2009/0312430 | A1 | 12/2009 | Sun et al. |
| 2011/0046227 | A1 | 2/2011 | Davis |
| 2011/0046228 | A1 | 2/2011 | Davis |
| 2011/0190397 | A1 | 8/2011 | Davis |
| 2015/0094322 | A1 | 4/2015 | Riel |
| 2015/0094323 | A1 | 4/2015 | Riel |

FOREIGN PATENT DOCUMENTS

| CN | 1939290 A | 4/2007 |
| CN | 101485637 A | 7/2009 |
| CN | 101485638 A | 7/2009 |
| CN | 101536990 A | 9/2009 |
| CN | 101732274 A | 6/2010 |
| JP | 2000034224 A | 2/2000 |
| JP | 2005523885 A | 8/2005 |
| JP | 2011140498 A | 7/2011 |
| JP | 2012519725 A | 8/2012 |
| JP | 2012236846 A | 12/2012 |
| JP | 2013510873 A | 3/2013 |
| WO | 1992015282 A2 | 9/1992 |
| WO | 2003054329 A | 7/2003 |
| WO | 2007048004 A2 | 4/2007 |
| WO | 2008131192 A2 | 10/2008 |
| WO | 2010046628 A1 | 4/2010 |
| WO | 2010103365 A | 9/2010 |
| WO | 2011060256 A | 5/2011 |
| WO | 2012100949 A1 | 8/2012 |
| WO | 2012100949 A | 9/2012 |
| WO | 2013155478 A1 | 10/2013 |
| WO | 2014066944 A1 | 5/2014 |

OTHER PUBLICATIONS

Adler et al., "Colchicine treatment for recurrent pericarditis: a decade of experience," Circulation, 97:2183-2185, 1998.
Antonopoulis et al., "Statins as Anti-inflammatory agents in Atherogenesis: Molecular mechanisms and lessons from the recent clinical trials," Curr. Pharma. Design, 18:1519-1530, 2012.
Crittenden, D., et al., "Colchicine Use Is Associated with decreased prevalence of Myocardial Infarction in Patients with Gout," J. Rheumatol., 39:1458-1464, 2012.
Finkelstein et al., "Colchicine for the prevention of Postpericardiotomy Syndrome," Herz, 27(8):791-794, 2002.
Gabrielyan, R.S., et al. "Comparative effects of losartan and losartan colchicines combination therapy in unstable angina patients with hyperuricaemia," Eur .J. Echocard., 7:S83, 2006.

(Continued)

*Primary Examiner* — Heidi Reese
(74) *Attorney, Agent, or Firm* — BioPharma Law Group, PLLC

(57) ABSTRACT

Methods of treating and/or preventing a cardiovascular event in a patient, the method comprising orally administering a colchicine to a patient who is receiving concurrent treatment with at least one antiplatelet agent, thereby treating and/or preventing the cardiovascular event in the patient are provided.

31 Claims, No Drawings

(56) References Cited

OTHER PUBLICATIONS

Hufford, C.D., et al., "(13)C- and (1)H-NMR. Assignments for Colchicine Derivatives," Helv.Chimica Acta, 63:50-56, 1980.
Imazio et al., "Colchicine as first-Choice therapy for recurrent pericarditis," Arch. Intern Med., 165(17):1987-1991, 2005.
Imazio et al., "Colchicine for recurrent pericarditis (CORP): a randomized trial," Ann. Intern. Med., 155(7):409-414, 2011.
Imazio et al., "Colchicine for the Prevention of the Post-pericardiotomy Syndrome (COPPS): a multicenter, randomized, double-blind, placebo-controlled trial," Eur. Heart J., 31:2749-2754, 2010.
Imazio et al., "Colchicine in addition to conventional therapy for acute pericarditis," Circulation, 112(13):2012-2016, 2005.
Imazio et al., "Colchicine prevents early postoperative pericardial and pleural effusions," Am. Heart J., 162(3):527-532, 2011.
International Preliminary report on Patentability for PCT/AU2013/001261 dated May 5, 2015.
Judkins, C., et al., "LoDoCo: Low Dose Colchicine in stable coronary artery disease and the effect on hs-CRP and brachial flow mediated dilation," Heart Lung Circ., 20S:S1-S155, Abstract 89, 2011.
Kouroupis, P., et al., "From Colchicine and some of its derivatives to 1,2,3,9,10-Pentamethoxybenzo[alpha]heptalenes," Helv. Chimica Acta, 78:1247-1277, 1995.
Lagrue, G., et al., "Effect of colchicine on atherosclerosis—I. Clinical and biological studies" Clin. Physiol. Biochem. 3:221-225, 1985.
Lee et al., "Pharmacokinetic comparison of sustained- and immediate-release oral formulations of cilostazol in healthy Korean subjects: a randomized, open-label, 3-part, sequential, 2-period, crossover, single-dose, food-effect, and multiple-dose study," Clin. Ther., 33(12):2038-53, 2011.
Maisch et al., "Guidelines on the Diagnosis and Management of Pericardial Diseases," Eur. Heart J., 25(7):587-610, 2004.
Malonne et al., "Pharmacokinetic evaluation of a new oral sustained release dosage form of tramadol," Brit. J. Pharmacol., 57(3):270-278, 2003.
Marcher, U., "Co-Processed Lactose-based excipients for Direct Compression," Meggle, Excipients & Technology, 2012.
Marcher, U., "Retalac, a new excipient for direct compression of sustained release formulations," http://www.pharmtech.com/meggle, Meggle, Jul. 9, 2010.
Nakamura, Y., et al., "Role of microtubules in ischemic preconditioning against myocardial infarction," Cardiovas. Res., 64:322-330, 2004.
Nidorf et al., "Low-dose colchicine for secondary prevention of cardiovascular disease," (The LoDoCo Trial) ACTR No. ACTR12610000293066, ethics approval at QII Jul. 2008.
Nidorf, S., et al., "Low-Dose Colchicine for secondary prevention of cariovascular disease," J. Am. Coll. Cardiol., 61:404-410, 2013.
O'Keefe Jr., J., et al., "Ineffectiveness of Colchicine for the prevention of Restenosis after coronary angioplasty," J. Am. Coll. Cardiol., 19:1597-1600, 1992.
Raju, N., et al., Effect of colchicine compared with placebo on high sensitivity C-reactive protein in patients with acute coronary syndrome or acute stroke: a pilot randomized controlled trial,: J. Thrombosis and Thrombolysis, 33:88-94, 2011.

Schlesinger, N., et al., "Canakinumab reduces the risk of acute gouty arthritis flares during initiation of allopurinol treatment: Results of a double-blind, randomized study", Animals Rheum. Dis. 70:1264-1271, 2011.
Seferovic, P., et al., "Management Strategies in Pericardial Emergencies", Herz, 31:891-900, 2006.
Siepmann et al., "Predicting drug release from HPMC/lactose tablets," Int. J. Pharmaceutics, 441:826-834, 2013.
Sparano, D.M. and R. Parker Ward, "Pericarditis and Pericardial Effusion: Management Update", Cardiovas. Med., 13:543-555, 2011.
Written Opinion and International Search Report for PCT Application No. PCT/IB2014/001201 dated Nov. 13, 2014.
Written Opinion and Search Report for PCT/AU2013/001261 dated Dec. 16, 2013.
Zema et al., "Different HPMC viscosity grades as coating agents for an oral time and/or site controlled delivery stystem: An investigation into the mechanisms governing drug release," J. Pharma. Sciences, 96(6):1527-1536, 2007.
Crittenden et al., "Colchicine Use Is Associated with decreased prevalence of Myocardial Infarction in Patients with Gout," J. Rheumatol., 39(7):1458-1464, 2012.
Gabrielyan et al. "516 comparative effects of losartan and losartan colchicines combination therapy in unstable angina patients with hyperuricaemia," European Journal of Echocardiography, 7:S83, 2006.
Hufford et al., "(13)C- and (1)H-NMR. Assignments for Colchicine Derivatives," Helvetica Chimica Acta, 63(1):50-56, 1980.
Judkins et al., "LoDoCo: Low Dose Colchicine in stable coronary artery disease and the effect on hs-CRP and brachial flow mediated dilation," CSANZ Abstracts 2011, pp. S36, Abstract No. 89.
Kouroupis et al., "From Colchicine and some of its derivatives to 1,2,3,9,10-Pentamethoxybenzo[alpha]heptalenes," Helvetica Chimica Acta, 78:1247-1277, 1995.
Lagrue et al., "Effect of colchicine on atherosclerosis—I. Clinical and biological studies" Clinical Physiology and Biochemistry, 3(5):221-225, 1985.
Nidorf et al., "Low-Dose Colchicine for secondary prevention of cariovascular disease," Journal of the American College of Cardiology, 61(4):404-410, 2013.
O'Keefe et al., "Ineffectiveness of 1-15 Colchicine for the prevention of Restenosis after coronary angioplasty," Journal of the American College of Cardiology, 19(7):1597-1600, 1992.
Raju et al., Effect of colchicine compared with placebo on high sensitivity C-reactive protein in patients with acute coronary syndrome or acute stroke: a pilot randomized controlled trial,: Journal of Thrombosis and Thrombolysis, 33(1):88-94, 2011.
Seferovic et al., "Management Strategies in Pericardial Emergencies", Herz, (31):891-900, 2006; CAPLUS 2007:184809.
Schlesinger et al., "Canakinumab reduces the risk of acute gouty arthritis flares during initiation of allopurinol treatment: Results of a double-blind, randomized study", Animals of the Rheumatic Diseases, 70(7):1264-1271, 2011.
Sparano et al., "Pericarditis and Pericardial Effusion: Management Update", Cardiovascular Medicine, 13(6):543-555, 2011.
Nakamura et al., "Role of microtubules in ischemic preconditioning against myocardial infarction," Cardiovascular Research, 64(2):322-330, 2004.
Nidorf et al., "Effect of Colchicine (0.5 mg Twice Daily) on High-Sensitivity C-Reactive Protein Independent of Aspirin and Atorvastatin in Patients with Stable Coronary Artery Disease," Am. J. Cardio., 99:805-807 2007.
International Preliminary Report on Patentability for PCT/IB2014/001201 dated Oct. 20, 2015, pp. 1-8.

METHOD OF TREATING CARDIOVASCULAR EVENTS USING COLCHICINE CONCURRENTLY WITH AN ANTIPLATELET AGENT

RELATED APPLICATION(S)

This application is a continuation of U.S. patent application Ser. No. 14/603,049, filed Jan. 22, 2015, which is a continuation-in-part of PCT Application No. PCT/AU2013/001261, filed Nov. 1, 2013, which claims the benefit of AU2012/904828, filed Nov. 2, 2012 and AU2012/904868, filed Nov. 5, 2012, the entire contents of which are incorporated herein by reference.

BACKGROUND OF THE INVENTION

Colchicine, chemical name (−)-N-[(7S, 12aS)-1,2,3,10-tetramethoxy-9-oxo-5,6,7,9-tetrahydrobenzo[a]heptalen-7-yl]-acetamide, is an alkaloid found in extracts of *Colchicum autumnale*, *Gloriosa superba*, and other plants. It is a microtubule-disrupting agent used in the treatment of conditions that may be treated, relieved or prevented with anti-inflammatory treatment.

Colchicine is well recognized as a valid therapy in acute flares of gouty arthritis, familial Mediterranean fever (FMF), Behçet's disease. It has also been used to treat many inflammatory disorders prone to fibrosis. In the recent past, colchicine has been proposed to be effective in therapy in cardiovascular diseases.

In particular, colchicine has been proposed as a first treatment option for recurrent pericarditis (class I indication) and optional for acute pericarditis (class IIa indication) in the 2004 European guidelines on the management of pericardial diseases (Maisch et al., *Guidelines on the Diagnosis and Management of Pericardial Diseases*, Eur Heart J., 2004, 25, 916-928).

Imazio et al. (*Circulation*, 2005, 112 (13), 2012-2016) showed that colchicine was effective for the treatment and the prevention of recurrent pericarditis in a prospective, randomized, open-label designed study of 120 patients with a first episode of acute pericarditis (idiopathic, viral, post-pericardiotomy syndromes, and connective tissue diseases), who were randomly assigned to conventional treatment with aspirin or conventional treatment plus colchicine (1.0 to 2.0 mg for the first day and then 0.5 to 1.0 mg/day for 3 months). The primary end point was recurrence rate, which was significantly reduced from 32.3% down to 10.7% at 18 months in the colchicine group (p=0.004).

Further, the same group showed that colchicine could be efficient after conventional treatment failure to manage acute pericarditis (Imazio at al., *Arch Intern Med*, 2005, 165 (17), 1987-91). In a prospective, randomized, open-label design, 84 consecutive patients with a first episode of recurrent pericarditis were randomly assigned to receive conventional treatment with aspirin alone or conventional treatment plus colchicine (1.0-2.0 mg the first day and then 0.5-1.0 mg/d for 6 months). The primary end point was the recurrence rate, which was significantly decreased in the colchicine group (actuarial rates at 18 months were 24.0% vs 50.6% with conventional treatment).

It has also been shown that colchicine is effective for secondary prevention of recurrent pericarditis Imazio et al., *Ann. Intern. Med.*, 2011, 155 (7), 409-14). Colchicine has also been proposed to reduce postpericardiotomy reactions revealed as pericarditis (Imazio et al., *Am. Heart J.*, 2011, 162 (3), 527-532; Meurin and Tabet, *Arch. Cardiovasc. Dis.*, 2011, 104 (8-9), 425-427).

Colchicine for the treatment of post-pericardiotomy syndrome (PPS) was tested for the first time in a preliminary prospective, open-label, randomized trial of colchicine (1.5 mg/day) compared with placebo beginning on the third post-operative day in 163 patients who underwent cardiac surgery (Finkelstein et al., *Herz*, 2002 27, 791-194).

The effectiveness of colchicine for the prevention of PPS has also been shown in a multicentre, double-blind, randomized trial, in which 360 patients (mean age 65.7+12.3 years, 66% males), 180 in each treatment arm, were randomized to receive placebo or colchicine (1.0 mg twice daily for the first day followed by a maintenance dose of 0.5 mg twice daily for 1 month in patients ≥70 kg, and halved doses for patients, 70 kg or intolerant to the highest dose) on the third post-operative day (Imazio et al., *European Heart Journal*, 2010, 31, 2749-2754).

In patients with atherosclerotic vascular disease, the diseased vessel wall is subject to injurious forces that promote plaque build-up and instability that may lead to coronary occlusion resulting in heart attack, ischemic stroke and sudden death. The response to injury within the diseased vessel is dependent on the architecture and content of atherosclerotic plaques. Lipid-rich plaques with a neo-vascular base are particularly susceptible to the effect of injury, which may leave them vulnerable to neutrophil infiltration. Neutrophils that enter the interstitial space may become activated upon exposure to the plaque contents, inciting an aggressive inflammatory response that may accelerate plaque instability increasing the risk of plaque enlargement and rupture and hence increasing the risk of clinical events.

Despite routine use of anti-platelet and statin therapy, patients with atherosclerotic vascular disease continue to be at risk of cardiovascular events, possibly because these treatments fail to target some of the inflammatory pathways implicated in the disease.

A number of additional treatments exist for the prevention or reduction in risk of coronary heart disease, including: antiplatelet agents (besides aspirin), anticoagulants, angiotensin-converting-enzyme inhibitors (ACEIs); aldosterone receptor antagonists (ARAB); beta-blockers calcium channel blockers and/or nitrates.

However, many of these treatments are recommended for acute conditions and do not address or provide for a long-term reduction in cardiovascular events in patients with clinically stable atherosclerotic vascular disease.

The present invention seeks to overcome, or at least ameliorate, one or more of the deficiencies of the prior art mentioned above, or to provide the consumer with a useful or commercial choice.

SUMMARY OF THE INVENTION

According to aspects of the invention illustrated herein, there is provided a method of treating and/or preventing a cardiovascular event in a patient, the method comprising administering a composition comprising an effective amount of colchicine to a patient who is receiving concurrent treatment with at least one antiplatelet agent, thereby treating and/or preventing the cardiovascular event in the patient.

According to embodiments of the invention, the patient has a coronary disease. According to embodiments of the invention, the coronary disease is a clinically stable coronary disease. According to embodiments of the invention, the cardiovascular event is acute coronary syndrome, outof-hospital cardiac arrest, and/or noncardioembolic ischemic stroke. According to embodiments of the invention, the antiplatelet agent is aspirin. According to embodiments of the invention, colchicine is included in an amount of 0.6 mg. According to embodiments of the invention, colchicine is included in an amount of 0.5 mg.

DETAILED DESCRIPTION OF THE INVENTION

I. Definitions

For the purposes of this invention, the term "colchicine" includes colchicine or any pharmaceutically acceptable salts thereof.

"Pharmaceutically acceptable" means that which is generally safe, non-toxic and neither biologically nor otherwise undesirable and includes that which is acceptable for veterinary use as well as human pharmaceutical use.

"Pharmaceutically acceptable salts" includes derivatives of colchicine, wherein the colchicine is modified by making acid or base addition salts thereof, and further refers to pharmaceutically acceptable solvates, including hydrates, and co-crystals of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the colchicine. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparaginate, glutamate, and the like; and combinations comprising one or more of the foregoing salts; organic amine salts such as triethylamine salt, pyridine salt, picoline salt, ethanolamine salt, triethanolamine salt, dicyclohexylamine salt, N,N' dibenzylethylenediamine salt, and the like; and amino acid salts such as arginate, asparaginate, glutamate, and the like; and combinations comprising one or more of the foregoing salts. All forms of such derivatives of colchicine are contemplated herein, including all crystalline, amorphous, and polymorph forms. Specific colchicine salts include colchicine hydrochloride, colchicine dihydrochloride, and co-crystals, hydrates or solvates thereof.

"Pharmacokinetic parameters" describe the in vivo characteristics of an active agent (or a metabolite or a surrogate marker for the active agent) over time, such as plasma concentration (C), Cmax, Cn, C24, Tmax, and AUC. "Cmax" is the measured plasma concentration of the active agent at the point of maximum, or peak, concentration. "Cmin" is the measured plasma concentration of the active agent at the point of minimum concentration. "Cn" is the measured plasma concentration of the active agent at about n hours after administration. "C24" is the measured plasma concentration of the active agent at about 24 hours after administration. The term "Tmax" refers to the time at which the measured plasma concentration of the active agent is the highest after administration of the active agent. "AUC" is the area under the curve of a graph of the measured plasma concentration of an active agent vs. time, measured from one time point to another time point. For example AUC0-t is the area under the curve of plasma concentration versus time from time 0 to time t, where t can be the last time point with measurable plasma concentration for an individual formulation. The AUC0-∞ or AUC0-INF is the calculated area under the curve of plasma concentration versus time from time 0 to time infinity. In steady-state studies, AUC0-τ is the area under the curve of plasma concentration over the dosing interval (i.e., from time 0 to time τ (tau), where tau is the length of the dosing interval. Other pharmacokinetic parameters are the parameter Ke or Kel, the terminal elimination rate constant calculated from a semi-log plot of the plasma concentration versus time curve; t½ the terminal elimination half-life, calculated as 0.693/Kel; CL/F denotes the apparent total body clearance after administration, calculated as Total Dose/Total AUC∞; and Varea/F denotes the apparent total volume of distribution after administration, calculated as Total Dose/(Total AUC∞×Kel).

"Efficacy" means the ability of an active agent administered to a patient to produce a therapeutic effect in the patient.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "dosage form" means a unit of administration of an active agent. Examples of dosage forms include tablets, capsules, injections, suspensions, liquids, emulsions, creams, ointments, suppositories, inhalable forms, transdermal forms, and the like.

An "immediate release formulation" refers to a formulation that releases greater than or equal to about 80% of the pharmaceutical agent in less than or equal to about 30 min.

For the purposes of this application, an enhancing agent ("enhancer") is defined as any non-pharmaceutically active ingredient that improves the therapeutic potential of a formulation.

"Sustained release" is defined herein as release of a pharmaceutical agent in a continuous manner over a prolonged period of time.

By "prolonged period of time" it is meant a continuous period of time of greater than about 1 hour, greater than about 4 hours, greater than about 8 hours, greater than about 12 hours, greater than about 16 hours, or up to more than about 24 hours.

As used herein, unless otherwise noted, "rate of release" or "release rate" or "dissolution rate" of a drug refers to the quantity of drug released from a dosage form per unit time, e.g., milligrams of drug released per hour (mg/hr) or a percentage of a total drug dose released per hour. Drug release rates for dosage forms are typically measured as an in vitro rate of drug release, i.e., a quantity of drug released from the dosage form per unit time measured under appropriate conditions and in a suitable fluid. The release rates referred to herein are determined by placing a dosage form to be tested in a medium in an appropriate dissolution bath. Aliquots of the medium, collected at pre-set intervals, are then injected into a chromatographic system fitted with an appropriate detector to quantify the amounts of drug released during the testing intervals.

Side effect is defined herein as a secondary and usually adverse effect of a drug.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on. The meaning of the terms "eukaryote", "animal", "mammal", etc. is well known in the art and can, for example, be deduced from Wehner and Gehring (1995; Thieme Verlag). In the context of this invention, it is also envisaged that animals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. In one embodiment, the subject/patient is a mammal; in another embodiment, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

II. Colchicine

In the following, colchicine used according to the present invention will be described in detail. The chemical structure of colchicine (Chem ID 2012) is as follows:

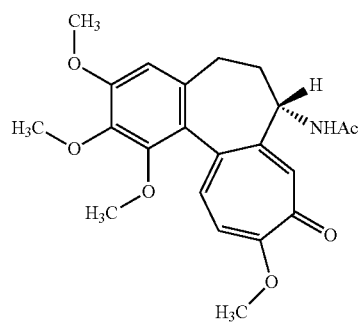 [SMILES: COc1cc2c(c(OC)c1OC)-c1ccc(OC)c(=O)cc1[C@@H](NC(C)=O)CC2]

The chemical name of colchicine is: N[5,6,7,9-tetrahydro-1,2,3,10-tetratmethoxy 9-oxobenzo[a]heptalen-7-yl], (S)-acetamide; molecular formula: $C_{22}H_{25}NO_6$; CAS number: 64-86-8.

Colchicine is an anti-inflammatory drug with a long history in human medicine, used for the symptomatic treatment of inflammatory diseases, most prominently gout. It is a natural product which can be extracted from two plants of the lily family, Colchicum autumnale and Gloriosa superba. Colchicine is a tricyclic alkaloid and has a molecular mass of 399.437. The active ingredient colchicine as well as its tablet formulation is listed in various national and international pharmacopeias such as the United States Pharmacopeia (USP).

The positive effect of its plant source in the treatment of rheumatism and swelling was described first already around 1500 B.C. in Egypt. Its use in gout was first described around 1500 years ago (Graham and Roberts, 1953, Ann Rheum Dis 12(1): 16-9). Today, the therapeutic value of colchicine is well established in a number of inflammatory diseases and approved by FDA for the prophylaxis and treatment of acute gout flares and familial Mediterranean fever (FMF). Other important established, though off-label uses are amongst others, Behçet's disease and recurrent pericarditis. In all known indications, it is generally administered orally as solid tablets in strengths of 0.5-0.6 mg/tablet (e.g. Europe and United States, respectively). The pharmacotherapeutic mechanism of action of colchicine in diverse disorders is not fully understood, though it is known that the drug accumulates preferentially in leucocytes, particularly neutrophils which is important for its therapeutic effect. Three major interactions of colchicine with specific proteins modulate its pharmacokinetics: tubulin, cytochrome P450 3A4 (CYP3A4), and P-glycoprotein. It is assumed that most therapeutic effects of the drug are related to its capacity to bind to β-tubulin, thus inhibiting self-assembly and polymerization of microtubules. Availability of tubulin is essential for several cellular functions such as mitosis. Therefore colchicine effectively functions as a "mitotic poison" or spindle poison. By inhibiting microtubule self-assembly, colchicine interferes with many cellular functions involved in the immune response such as modulation of the production of chemokines chemokines and prostanoids and inhibition of neutrophil and endothelial cell adhesion molecules. Eventually it decreases neutrophil degranulation, chemotaxis and phagocytosis, thus reducing the initiation and amplification of inflammation. Colchicine also inhibits uric acid crystal deposition (a process important to the genesis of gout), which is enhanced by a low pH in the tissues, probably by inhibiting oxidation of glucose and subsequent lactic acid reduction in leukocytes (Imazio, Brucato et al. 2009, Eur Heart J, 30(5): 532-9; Cocco, Chu et al. 2010, *Eur J Intern Med,* 21(6): 503-8; Stanton, Gernert et al. 2011, *Med Res Rev,* 31(3): 443-81). In the management of pericarditis, colchicine excerpts its therapeutic effect by suppressing the acute pericardial inflammation. However, the exact cellular and molecular mechanisms of how colchicine relieves pain and inflammation in acute pericarditis and prevents recurrences are not fully understood.

Colchicine in the context of the present invention can be used for the prevention and/or treatment of cardiovascular diseases and/or inflammatory diseases.

III. Treatment Methods Using Colchicine Concurrently with an Antithrombotic Agent The present invention also presents a method of treatment or prevention of cardiovascular diseases, cardiovascular events and/or inflammatory disorders in a subject, comprising administering to the subject a therapeutically effective amount of colchicine of the present invention, wherein colchicine is administered concurrently with at least one antithrombotic agent. There are three classes of antithrombotic drugs, including anticoagulants, antiplatelet agents, and thrombolytic agents. As used herein, the term "anticoagulants" refers to drugs that slow down clotting, thereby reducing fibrin formation and preventing clots from forming and growing. Examples of anticoagulants include, but are not limited to, novel oral anticoagulants (NOACs) (including dabigatran, rivaroxaban, and apixaban), coumarins (vitamin K antagonists) (including warfarin (Coumadin), acenocoumarol and phenprocoumon, atromentin, brodifacoum, phenindione), heparin and derivatives, low molecular weight heparin (including dalteparin and enoxaparin), synthetic pentasaccharide inhibitors of factor Xa, direct factor Xa inhibitors (including rivaroxaban, apixaban, edoxaban, and darexaban), direct thrombin inhibitors (including hirudin, lepirudin, bivalirudin, ximelagatrain), and antithrombin protein therapeutics. As used herein, the term "antiplatelet agent" refers to drugs that prevent platelets from clumping and also prevent clots from forming and growing. Examples of antiplatelet agents include, but are not limited to, irreversible cyclooxygenase inhibitors (including aspirin and triflusal), adenosine diphosphate (ADP) receptor inhibitors (including clopidogrel, prasugrel, ticagrelor and ticlopidine), phosphodiesterase inhibitors (including cilostazol), protease-activated receptor-1 (PAR-1) antagonists (including vorapaxar), glycoprotein IIB/IIIA inhibitors (including abciximab, eptifibatide, tirofiban), adenosine reuptake inhibitors (including dipyridamole), and thromboxane inhibitors (including thromboxane synthase inhibitors and thromboxane receptor antagonists such as terutroban. As used herein, the term "thrombolytic agent" refers to drugs that are able to dissolve a clot (thrombus) and reopen an artery or vein. Thrombolytic agents are used for the treatment of myocardial infarction (heart attack), thromboembolic strokes, deep vein thrombosis and pulmonary embolism to clear a blocked artery and avoid permanent damage to the perfused tissue (e.g. myocardium, brain, leg) and death. Examples of thrombolytic agents include, but are not limited to, tissue plasminogen activator (t-PA), e.g., alteplase, reteplase, tenecteplase; anistreplase; streptokinase; and urokinase.

In one embodiment, the present invention can be used to treat cardiovascular diseases and/or inflammatory disorders, including, but not limited to, acute vascular diseases, such as myocardial infarction, stroke, peripheral arterial occlusion, deep vein thrombosis, pulmonary embolism, and other blood system thrombosis. Such disorders are caused by either partial or total occlusion of a blood vessel by a blood clot, which consists of fibrin and platelet aggregates. Therapeutic intervention with colchicine concurrently with at least one agent that prevents or delays clot formation (i.e., anticoagulants and antiplatelet agents) or with an agent that dissolves blood clots may, in one embodiment, effectively slow clot formation and enhance clot dissolution in blood. In another embodiment, administering colchicine concurrently with at least one antithrombotic agent may delay clotting time and/or may change the character of the clot that is formed to a looser, less stable clot. Accordingly, administering colchicine concurrently with at least one antithrombotic agent is useful in the treatment of cardiovascular and/or thrombotic disorders, for dissolving or lysing clots in cardiovascular and/or thrombotic patients, for delaying or inhibiting hard clot formation or supplementing cardiovascular and/or thrombolytic therapy in the patients.

According to the present invention, colchicine as described herein is administered in the form of a sustained release preparation or in an immediate release formulation. An example of a sustained release formulation of colchicine can be found in PCT/IB2014/001201 (WO2014/170755), which is hereby incorporated by reference in its entirety. An example of an immediate release formulation is any commercially available immediate release formulation of colchicine.

"Concurrent administration," or "co-administration" or "co-treatment," as used herein includes administration of the agents, in conjunction or combination, together, or before or after each other. It can also refer to administering the agents in a fixed combination such as in a single dosage form (i.e., one pill or tablet). In one embodiment of the present invention, colchicine can be administered with at least one antithrombotic agent in a single dosage form. Providing the therapeutic agents in a single dosage form (i.e., one pill or tablet) has the effect of reducing the number of medications that a patient takes in one day, which can improve patient adherence to the treatment regimen.

Conventional antithrombotic agents are expected to be administered in dosages and by routes consistent with the usual clinical practice. The typical dosages and administration regimens for some of these antiplatelet, anticoagulant and thrombolytic agents, when administered as monotherapy, are discussed below. Naturally, these dosages may vary as determined by good medical practice and the clinical condition of the individual patient. The daily dosage amount of aspirin may vary from patient to patient. Some patients, for example, may only require very low doses of aspirin, such as 75 mg daily, which is less than a standard infant aspirin dose. Other patients may receive a daily dosage amount from 81 mg, the amount in an infant aspirin, to 325 mg, the amount in a regular strength tablet. The daily dosage amount of warfarin must be individualized according to the patient's sensitivity to the drug as indicated by its effect on the prothrombin time (PT) ratio. The loading dose is typically 2 to 5 mg/day and most patients are satisfactorily maintained at a dose of 2 to 10 mg/day. Warfarin is generally given orally but may be administered intravenously if the patient cannot take the drug orally. The daily dosage amount of clopidogrel must also be individualized according to the patient's sensitivity to the drug as well as to any other medications the patient is taking. The loading dose is typically 300 mg/day and the daily dose is generally between 75 mg and 100 mg.

When colchicine is concurrently administered with at least one antithrombotic agent, the colchicine and the antithrombotic agent may each be administered in amounts that would be sufficient for monotherapeutic effectiveness, or they may be administered in amount less than what would be sufficient for monotherapeutic amounts, referred to herein as the "adjusted daily dosage amount". In one embodiment, colchicine may be capable of improving the therapeutic effectiveness of existing anticoagulant or thrombolytic agents, which would reduce the dosages of colchicine and/or the antithrombotic agent needed to exert their desired anticoagulant or thrombolytic effects. This reduction of dosage amount would, in turn, decrease the risk of adverse side effects associated with the use of thrombolytic agents, including, for example, undesirable internal or external bleeding. The use of colchicine may further improve the therapeutic effectiveness of the other antithrombotic agents in a variety of ways. For example, lowering the dosage of the antithrombotic agent required for therapeutic effectiveness reduces toxicity and/or cost of treatment, and thus allows wider use of the agent. Alternatively, concurrent administration may produce an increased, more rapid or more complete anticoagulant or thrombolytic effect than could be achieved with either agent alone.

In accordance with one embodiment of the present invention, when colchicine is concurrently administered with at least one antithrombotic agent, the daily dosage amount of colchicine may be between 25% and 75% of the daily dosage amount of colchicine when colchicine is administered in the absence of at least one antithrombotic agent. In one embodiment, if the daily dosage amount of colchicine is 0.6 mg, then the adjusted dosage daily amount of colchicine used concurrently with at least one antithrombotic agent may be between about 0.15 mg to about 0.45 mg. In another embodiment, if the daily dosage amount of colchicine is 0.55 mg, then the adjusted dosage daily amount of colchicine used concurrently with at least one antithrombotic agent may be between about 0.13 mg to about 0.43 mg. In one embodiment, if the daily dosage amount of colchicine is 0.5 mg, then the adjusted dosage daily amount of colchicine used concurrently with at least one antithrombotic agent may be between about 0.10 mg to about 0.40 mg.

In accordance with another embodiment of the present invention, when colchicine is concurrently administered with at least one antithrombotic agent, the daily dosage amount of the antithrombotic agent may be between 25% and 75% of the daily dosage amount of the antithrombotic agent when the antithrombotic agent is administered in the absence of colchicine.

In one embodiment, treatment includes the application or administration of a colchicine formulation as described herein to a patient, where the patient has, or has the risk of developing a cardiovascular disease and/or an inflammatory disorder. In another embodiment, treatment is also intended to include the application or administration of a pharmaceutical composition comprising the colchicine formulation, to a patient, where the patient has, or has the risk of developing a cardiovascular disease and/or inflammatory disorder.

As used herein, the term "cardiovascular disease" refers to any disease involving the heart and/or the vascular system (all blood vessels incl. arteries, capillaries and veins). This includes all diseases listed in chapter IX "Diseases of the circulatory system (I00-I99)" of the International Statistical Classification of Diseases and Related Health Problems 10th Revision (ICD-10) Version for 2010, by the World Health Organisation.

More specifically, all diseases of this ICD-10 class which involve a) inflammation of any part of the heart or blood vessel as well as b) ischemia/atherosclerosis/thickening of any blood vessel of the circulatory system.

Colchicine as described herein is for use in the treatment and/or prevention of any inflammatory disorder involving the heart tissue selected from ICD-10 sections I00-I99. More specifically, these include acute and recurrent pericarditis as well as post-surgical complications involving inflammation of the pericardium (Postcardiotomy syndrome, Postpericardiotomy syndrome, pericardial effusion). Other inflammatory heart diseases covered are any form of myocarditis, endocarditis and arterial fibrillation.

The proposed mechanism of action in this indication is the inhibition of plaque instability by neutrophil inhibition. In stable coronary disease, fatty materials accumulate at the blood vessel and form a stable plaque. This plaque may become subject to attack by neutrophils. This may cause plaque instability and consequently leads to plaque rupture and clinical events. Therefore, colchicine as described herein is for use in treatment and/or prevention of any disease of the cardiovascular system which involves ischemia, atherosclerosis and/or thickening of blood vessels (arteries, capillaries, veins) due to plaque formation with a risk of clinical events due to plaque instability. Claimed are all diseases classified in ICD-10 section I00-I99 fulfilling any of these requirements. Examples are stable coronary disease, cardiovascular atherosclerosis, and atherosclerosis of the peripheral vascular system, Abdominal Aortic Aneurysm (AAA) and carotid and iliofemoral/renal atheromas (e.g. I25, I70).

In the context of the present invention, an acute cardiovascular event in a patient with stable cardiovascular disease is preferably a cardiovascular event in a patient with stable coronary disease. In the context of the present invention, the term "stable coronary disease" and "stable coronary heart disease" have the same meaning and are used interchangeable. Both terms include the medical condition stable coronary artery disease (SCAD). "Stable" in the context of the terms "stable cardiovascular disease", "stable coronary disease" or "stable coronary heart disease" is defined as any conditions of diagnosed cardiovascular disease in the absence of acute cardiovascular events. Hence, e.g. stable coronary disease defines the different evolutionary phases of coronary disease, excluding the situations in, which coronary artery thrombosis dominates clinical presentation (acute coronary syndrome).

Colchicine in the context of the present invention can be used for the prevention and/or treatment of cardiovascular diseases and/or cardiovascular events. Cardiovascular diseases include, but are not limited to, heart diseases as described, e.g., in Robbins and Cotran, Pathologic Basis of Disease, Eighth Edition, Saunders Elsevier. Cardiovascular disease refers to a group of diseases of the circulatory system including the heart, blood and lymphatic vessels. In particular, cardiovascular disease may include vascular diseases involving atherosclerosis, plaque formation or disposition. The most common cardiovascular diseases are coronary heart disease and stroke. Non-limiting examples of cardiovascular disease which may be prevented or treated according to the methods of the invention include coronary heart disease (disease of the blood vessels supplying the heart muscle), cerebrovascular disease (disease of the blood vessels supplying the brain), peripheral arterial disease (disease of blood vessels supplying the arms and legs), rheumatic heart disease (damage to the heart muscle and heart valves from rheumatic fever, caused by streptococcal bacteria), congenital heart disease (malformations of heart structure existing at birth), deep vein thrombosis and pulmonary embolism (blood clots in the leg veins, which can dislodge and move to the heart and lungs), hyperlipemia (an excessive level of blood fats, such as LDL), high blood pressure, coronary artery disease, atherosclerosis, ischemic diseases, abdominal aortic aneurism, carotid and iliofemoral/renal atheromas, heart failure, cardiac rhythm defects, arteriosclerosis, heart attack and stroke. Heart attacks and strokes are usually acute events and are mainly caused by a blockage that prevents blood from flowing to the heart or brain. The most common reason for this is a build-up of fatty deposits on the inner walls of the blood vessels that supply the heart or brain. Strokes can also be caused by bleeding from a blood vessel in the brain or from blood clots.

Especially, in the context of the present invention, colchicine concurrently with at least one antithrombotic agent can be used for the prevention of acute pericarditis, recurrent pericarditis, recurrent pericarditis in patients with a history of pericarditis, post-pericardiotomy syndrome (PPS), PPS in patients undergoing cardiac surgery, and cardiovascular events in patients with stable coronary (heart) disease (the cardiovascular events can be acute cardiovascular events).

Pericarditis is an inflammatory disease involving the pericardium, a thin double-walled fibroelastic sac, surrounding the heart. Due to inflammation, it comes to irritation and swelling of the pericardium. This causes the sac to rub against the heart which causes chest pain, the most common symptom of pericarditis. Pericarditis is the most common form if inflammatory disorder of the heart, though very rare on a population basis. Pericarditis is very heterogeneous in its origin, clinical manifestations and duration of symptoms. It can either occur as isolated clinical problem or as a manifestation of a systemic disease. In most cases (90%), pericarditis is of idiopathic (spontaneous, unknown) etiology but may also occur secondary to systemic infections, acute myocardial infarction or autoimmune diseases. The post-pericardiotomy syndrome (PPS) may be a troublesome complication following cardiac surgery occurring a few days to several weeks after the surgical operation. The estimated incidence of the syndrome has a relatively wide range affecting from 10 to 40% of patients submitted to cardiac surgery (Prince and Cunhe, 1997, *Heart Lung*, 26:165).

Non-limiting examples of (acute) cardiovascular events are injury of the atherosclerotic wall, acute coronary syndrome, out-of-hospital cardiac arrest, or non-cardioembolic ischemic stroke. Further such events are described, e.g., in Robbins and Cotran, Pathologic Basis of Disease, Eighth Edition, Saunders Elsevier. In some contexts, the cardiovascular event is not acute pericarditis. In some contexts, the cardiovascular event is not recurrent pericarditis.

In an embodiment, the use of colchicine concurrently with at least one antithrombotic agent may be used to treat inflammatory disease other than those mentioned above. In an embodiment, the inflammatory disease includes, but is not limited to, gout, familial Mediterranean fever, Behcet's disease, Age-related macular degeneration and Alzheimer's disease.

Patients/subjects which suffer from the above described disease and/or which are suitable for treatment with colchicine according to the present invention can be diagnosed by conventional and/or routine procedures. The skilled person is well aware of them. Diagnosis is also described, e.g., in Robbins and Cotran, Pathologic Basis of Disease, Eighth Edition, Saunders Elsevier.

In an embodiment, the use of colchicine concurrently with at least one antithrombotic agent as described herein is useful for the treatment of various cardiovascular diseases, cardiovascular events and/or inflammatory disorders. In some embodiments, treatment of a cardiovascular disease, cardiovascular event and/or an inflammatory disorder is intended to include remediation of, improvement of, amelioration of, lessening of the severity of, or reduction in the time course of, a disease, disorder or condition, or any parameter or symptom thereof. In an embodiment of the present invention, the term "disorder", "disease", or "condition" is to be understood as cardiovascular disease and/or inflammatory disorder as described above. In the context of the present invention, "amelioration" refers, without limitation, to any observable beneficial effect.

In accordance with the present invention, the colchicine formulation herein can be used to promote a positive therapeutic response with respect to the cardiovascular disease and/or inflammatory disorder. A "positive therapeutic response" with respect to the cardiovascular disease and/or inflammatory disorder is intended to include an improvement in the disease can be evidenced by, for example, a delayed onset of clinical symptoms of the disease or condition, a reduction in severity of some or all clinical symptoms of the disease or condition, a slower progression of the disease or condition, an improvement in the overall health or well-being of the subject, or by other parameters well known in the art that are specific to the particular disease.

In another embodiment, the use of colchicine concurrently with at least one antithrombotic agent as described herein is useful in the prevention of various cardiovascular diseases, cardiovascular events and/or inflammatory disorders. In the context of the present invention, the term "prevention" is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician. Prevention includes, without limitation, to avoid the disease or condition from occurring in patient and/or subject that may be predisposed to the disease but does not yet experience or exhibit symptoms of the disease (prophylactic treatment).

The use of colchicine concurrently with at least one antithrombotic agent according to the present invention may also be used concurrently with other conventional therapies for any of the diseases disclosed herein. Such conventional therapies are well known in the art and the skilled person knows any such therapies. Colchicine concurrently with at least one antithrombotic agent as described herein may also be used concurrently with colchicine-compatible statins. In general, non-limiting examples of statins are atorvastatin (Lipitor®, Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). In connection with the present invention, colchicine-compatible statins are used. Preferably, in the context of the present invention, the combination of the composition of the present invention with the colchicine-compatible statins are accomplished in connection with stable coronary heart disease. Such statins preferably are statins which, due to the nature of their mechanism of action, metabolism and/or clearance do not, or only to a small extent, interfere with the mechanism of action, metabolism and/or clearance of colchicine and therefore show a reduced risk, severity and/or incidence of drug-related drug adverse events when given concurrently with colchicine.

In an embodiment, the use of colchicine is in fixed (within the same pharmaceutical preparation) or unfixed (different pharmaceutical preparation) combination. "Fixed combination" is to be understood as meaning a combination whose active ingredients are combined at fixed doses in the same vehicle (single formula) that delivers them together to the point of application. Fixed combination can mean, e.g., in a single tablet, solution, cream, capsule, gel, ointment, salve, patch, suppository or transdermal delivery system. "Unfixed combination" as used herein is to be understood as meaning that the active ingredients/components are in more than one vehicle (e.g. tablets, solutions, creams, capsules, gels, ointments, salves, patches, suppositories or transdermal delivery systems). Each of the vehicles can contain a desired pharmaceutical composition or active component. For example, a preferred unfixed combination as described herein means that one vehicle contains colchicine, as described herein, and another vehicle contains a colchicine-compatible statin, as described herein. Examples of colchicine as described herein in fixed or unfixed combination(s) encompass(es) colchicine concurrently with one or more colchicine-compatible statins selected from the group consisting of atorvastatin, rosuvastatin, simvastatin and pravastatin. Specifically, colchicine as described herein in fixed or unfixed combination is to be understood as meaning colchicine concurrently with atorvastatin. Specifically, colchicine as described herein in fixed or unfixed combination is to be understood as meaning colchicine concurrently with rosuvastatin. Specifically, colchicine as described herein in fixed or unfixed combination is to be understood as meaning colchicine concurrently with simvastatin. Specifically, colchicine as described herein in fixed or unfixed combination is to be understood as meaning colchicine concurrently with pravastatin.

In some embodiments, the use of colchicine concurrently with at least one antithrombotic agent as described herein may be used concurrently with a statin and another agent, such as ezetimibe/simvastatin. Colchicine as described herein may be used concurrently with other drugs, e.g, which are used in medicine and are known to the skilled person (e.g. antibiotics, NSAID (non-steroidal anti-inflammatory drugs), corticosteroids).

VI. Administration Methods

Methods of preparing and administering colchicine of the present invention to a subject in need thereof are well known to or are readily determined by those skilled in the art. The route of administration of the colchicine formulation can be, for example, oral, parenteral, by inhalation or topical. The term parenteral as used herein includes, e.g., intravenous, intraarterial, intraperitoneal, intramuscular, subcutaneous, rectal, or vaginal administration.

Colchicine when used as a composition in the context of the present invention may include one or more pharmaceutically acceptable carriers and thus may be prepared in the form of a local formulation, in order for it to be administered. The pharmaceutically acceptable carrier may include saline, sterile water, linger liquid, buffer saline, a dextrose solution, a malto dextrin solution, glycerol, ethanol and mixtures of one or more thereof, and also may include an additive such as an antioxidant, a buffer, a bacteriostatic agent or the like, as necessary. Furthermore, a diluent, a dispersant, a surfactant, a binder and a lubricant may be added when the composition according to the present invention is prepared, e.g., in the form of a local formulation such as an ointment, lotion, cream, gel, skin emulsion, skin suspension, patch or spray.

Non-limiting examples for administration of the compound and or compositions according to the present invention include coated and uncoated tablets, soft gelatine capsules, hard gelatine capsules, lozenges, troches, solutions, emulsions, suspensions, syrups, elixirs, powders and granules for reconstitution, dispersible powders and granules, medicated gums, chewing tablets and effervescent tablets. The composition according to the present invention can administered in any pharmaceutical form for oral (e.g. solid, semi-solid, liquid), dermal (e.g. dermal patch), sublingual, parenteral (e.g. injection), ophthalmic (e.g. eye drops, gel or ointment) or rectal (e.g. suppository) administration. In an embodiment, the composition is formulated as a tablet, capsule, suppository, dermal patch or sublingual formulation.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of the colchicine formulation to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In some situations, the composition of the present invention can be parenterally administered. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

Parenteral formulations can be a single bolus dose, an infusion or a loading bolus dose followed with a maintenance dose. These compositions can be administered at specific fixed or variable intervals, e.g., once a day, or on an "as needed" basis.

The composition according to the present invention may be administered in a dose range varying depending on the patient's body weight, age, gender, health condition, diet, administration time, administration method, excretion rate and disease severity. The compounds of the present invention as compounds per se in their use as pharmacophores or as pharmaceutical compositions can be administered to the patient and/or subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition comprising the herein defined should be, e.g., in a range as described below. Progress can be monitored by periodic assessment.

The composition according to the present invention can be administered with a single dose or with 2, 3, 4, 5, 6, 7, 8, 9, or 10 doses, if desired. The composition can be administered 1, 2, 3, 4, 5, 6, 7, 8, 9 or 10 times per day. Preferably, colchicine according to the present invention is administered once per day. More preferably, colchicine according to the present invention is administered once per day as a single dose.

The composition according to the present invention can be administered regularly for long periods of time. In an embodiment, the composition can be administered regularly for 1, 2, 3, 4, 5, 6, 7, 8, 9, 10 or more years. In another embodiment, the composition can be administered regularly for 1, 2, 3, 4, 5, 6, 7, 8, 9, 10, 11, 12 or more months. In other embodiments, the composition can be administered regularly for 1, 2, 3, 4, 5, 6, 7, 8, 9, 10 or more weeks. As used herein, the term "regularly" refers to administration of the composition at regular times or intervals over a period of time. For instance, the composition may be administered to a patient once daily for three years. In other embodiments, the composition may be administered to a patient once every other day for 5 years. It should be appreciated that the frequency of administration may vary based on a number of factors, including, but not limited to, the severity of disease, the overall health of the patient, any additional medications the patient is taking, and whether the treatment is prophylactic or not. It should also be appreciated that the frequency of administration may be adjusted at any point.

The amount/concentration/dose of the composition according to the present invention can be between 0.1 mg and 5.0 mg, 0.1 mg and 2.0 mg, 0.1 mg to 1.5 mg, 0.1 mg to 1.0 mg, 0.1 mg to 0.75 mg, 0.1 mg to 0.5 mg, 0.25 mg to 5.0 mg, 0.25 mg to 2.0 mg, 0.25 mg to 1.5 mg, 0.25 mg to 1.0 mg, 0.25 mg to 0.75 mg or 0.25 mg to 0.5 mg. In an embodiment, the composition according to the present invention is administered at a daily dose of colchicine of between about 0.1 mg and about 0.75 mg or between about 0.1 mg and about 0.5 mg. In another embodiment, the composition according to the present invention is administered at a daily dose of colchicine of between about 0.25 mg to about 0.75 mg or between about 0.25 mg to about 0.5 mg. In an embodiment, the composition according to the present invention is administered at a daily dose of about 0.5 mg colchicine.

In a preferred embodiment, the amount/concentration of colchicine as used herein can be administered at the first day of administration in a higher dose (concentration/amount) compared to the administration of colchicine at the following days(s) of administration (maintenance administration/maintenance dose of administration). Alternatively such decreased dose (maintenance dose) can be started after 2, 3, 4, 5, 6, 7, 8, 9 or 10 days of initial administration of the higher dose. In case the course of treatment is any such as described above, the higher dose/amount/concentration of colchicine (e.g. at the first day of administration) can be any as described above, provided that the maintenance dose (the dose/amount/concentration of colchicine at the days following the higher dose/amount/concentration) is lower than the initial dose/amount/concentration of colchicine (e.g. at the first day of administration). Preferably, the composition of the invention is administered with a dose of colchicine of between about 1.0 mg to about 2.0 mg at the first day (preferably as a single dose) of administration and the maintenance dose of colchicine at the following day(s) of administration is between about 0.5 mg to about 1.0 mg.

In keeping with the scope of the present disclosure, the colchicine formulation of the present invention can be administered to a human or other animal in accordance with the aforementioned methods of treatment in an amount sufficient to produce a therapeutic effect. The colchicine formulation can be administered to such human or other animal in a conventional dosage form prepared by combining the colchicine formulation of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

By "therapeutically effective dose or amount" or "effective amount" is intended an amount of the colchicine formulation that when administered brings about a positive therapeutic response with respect to treatment of a patient with a disease to be treated, e.g., an improvement in the disease can be evidenced by, for example, a delayed onset of clinical symptoms of the disease or condition, a reduction in severity of some or all clinical symptoms of the disease or condition, a slower progression of the disease or condition, an improvement in the overall health or well-being of the subject, or by other parameters well known in the art that are specific to the particular disease. In an embodiment, a therapeutically effective dose amount of the composition according to the present invention can be between 0.1 mg and 5.0 mg, 0.1 mg and 2.0 mg, 0.1 mg to 1.5 mg, 0.1 mg to 1.0 mg, 0.1 mg to 0.75 mg, 0.1 mg to 0.5 mg, 0.25 mg to 5.0 mg, 0.25 mg to 2.0 mg, 0.25 mg to 1.5 mg, 0.25 mg to 1.0 mg, 0.25 mg to 0.75 mg or 0.25 mg to 0.5 mg. In an embodiment, the therapeutically effective dose amount of the composition according to the present invention is administered at a daily dose of colchicine of between about 0.1 mg and about 0.75 mg or between about 0.1 mg and about 0.5 mg. In another embodiment, the therapeutically effective dose amount of the composition according to the present invention is administered at a daily dose of colchicine of between about 0.25 mg to about 0.75 mg or between about 0.25 mg to about 0.5 mg. In an embodiment, the therapeutically effective dose amount of the composition according to the present invention is administered at a daily dose of about 0.5 mg colchicine.

The invention also provides for the use of the colchicine formulation in the manufacture of a medicament for treating a subject for treating a cardiovascular disease, cardiovascular event and/or inflammatory disorder, wherein the medicament is used in a subject that has been pretreated or is concurrently being treated with at least one other therapy. By "pretreated" or "pretreatment" is intended the subject has received one or more other therapies prior to receiving the medicament comprising the colchicine formulation. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the colchicine formulation. By "concurrent" or "concomitant" is intended the subject is receiving one or more other therapies while at the same time receiving the medicament comprising the colchicine formulation. It is not necessary that the subject was a responder to pretreatment with the prior therapy or therapies or a responder to the concurrent therapy or therapies. Thus, the subject that receives the medicament comprising the colchicine formulation could have responded, or could have failed to respond, to pretreatment with the prior therapy, or to one or more of the prior therapies where pretreatment comprised multiple therapies.

All of the references cited above, as well as all references cited herein, are incorporated herein by reference in their entireties.

While the invention has been illustrated and described in detail in above, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Therapeutic Effects of an Immediate Release Formulation in Patients with Cardiovascular Disease To assess the therapeutic effects of an immediate release formulation in patients with cardiovascular disease, a prospective randomized observer blinded end-point trial was conducted to determine whether adding 0.5 mg/day of colchicine to standard secondary prevention therapies including aspirin and high dose statins reduces the risk of cardiovascular events in patients with objectively diagnosed and clinically stable coronary disease. This study is described in PCT/AU2013/001261 and is hereby incorporated in its entirety by reference.

Study Conduct and Design:

The LoDoCo Trial was conducted under the auspices of the Heart Research Institute of Western Australia. It was designed by the principal investigators, registered with the Australian Clinical Trial Registry (12610000293066), and received ethics approval from the Human Research Ethics Committee at Sir Charles Gairdner Hospital Perth Western Australia in July 2008. There was no external funding source.

The study had a prospective randomized, open, blinded end-point design. Eligible consenting patients with established coronary disease presenting for routine clinical review were randomized to receive colchicine 0.5 mg/day or no colchicine without any other change to their medical therapy. All outcomes were evaluated by an experienced adjudicator blinded to the treatment allocation.

Study Size and Eligibility:

It was planned to recruit a study population that would include 500 patients planned (532 patients randomized as 32 dropped out early), 250 randomized to the control group and 250 patients randomized to treatment who were tolerant of colchicine for at least 4 weeks after the date of their randomization. Patients were eligible for inclusion if they met each of the following criteria: 1) angiographically proven coronary disease; 2) aged 35 to 85 years; 3) clinically stable for at least 6 months, 4) no major competing co-morbidities or contra-indication to colchicine therapy, 5) considered to be compliant with therapy and attending routine cardiology follow up appointments, and 6) willing to be consented and randomized into the study. Patients with a history of bypass surgery were only eligible if they had undergone bypass surgery more than 10 years before, or had angiographic evidence of graft failure or had undergone stenting since their bypass surgery. All patients signed informed consent before randomization.

Randomization:

The randomization sequence was computer generated, kept concealed from the investigators at all times and was managed by a research assistant who had no involvement in the evaluation or management of study patients. Once the assistant received the consent form, the patients' demographic data were entered into the data base and the investigators and patients were advised in writing of the treatment group to which the patient had been assigned. Despite electing to use the lowest dose of colchicine available, it was anticipated that a number of patients would withdraw from therapy early after randomization due to gastrointestinal side effects. In order to ensure that the requisite number of patients in the treatment arm were actually tolerant of treatment, the protocol allowed for the research assistant to assign a newly recruited patient to treatment if a patient discontinued colchicine due to side effects in the first month. Patients who were intolerant to therapy remained in the study, and were followed in the usual manner and included in the primary intention to treat analysis.

Intervention:

Patients randomized to active treatment were given a prescription for colchicine 0.5 mg daily by their referring cardiologist. The drug was dispensed by their usual chemist, and if requested, patients were reimbursed for the cost of these scripts. All other treatments were continued as usual.

Follow-Up and Definition of Clinical Outcomes:

Patient compliance with treatment and outcome data were collected at routine follow up visits and at the time of any unplanned hospital admission. An acute coronary syndrome (ACS) was defined as either (a) Acute Myocardial Infarction (AMI), as evidenced by acute ischemic chest pain associated with a rise in serum troponin above the upper limit of normal or (b) Unstable Angina (UA), as evidenced by a recent acceleration of the patient's angina unassociated with a rise in serum troponin but associated with angiographic evidence of a change in the patient's coronary anatomy. (Unstable Angina Braunwald classification types IB and IIB). The ACS was characterized as being stent-related if there was evidence of significant in-stent stenosis or acute stent thrombosis. Out of Hospital Cardiac Arrest was defined as either a sudden death as evidenced on the patient's death certificate, or a non-fatal out of hospital cardiac arrest, defined as a recovery from sudden collapse associated with documented asystole, ventricular tachycardia or ventricular fibrillation. Noncardio-embolic ischemic stroke was defined as CT or MRI proven ischemic stroke adjudged by the treating neurologist as not being due to atrial fibrillation or intracranial hemorrhage.

The primary efficacy outcome was the present of a cardiovascular event such as ACS, fatal or non-fatal out of hospital cardiac arrest or non-cardio-embolic ischemic stroke. Secondary outcomes were (a) individual components of the primary outcome, and (b) the components of ACS unrelated to stent disease.

Timelines:

The pre-specified study duration was a minimum follow up of two years in all patients. Accordingly the study was closed on May 31, 2012. During May, all living patients were contacted by phone to collect compliance and outcome data from the last date of follow-up. Final outcome data were available in all patients and no patients were lost to follow up.

Statistical Power:

Assuming that the control group had a combined cardiovascular event rate (ACS, out of hospital cardiac arrest or non cardio-embolic-ischemic stroke) of 8%, an accrual interval of 2 years and a follow-up after the accrual interval of 2 years, the planned sample size provided >80% power to detect a hazard ratio of <0.50 based on a two sided significance level of 5%.

Data Analysis:

Summary statistics, including mean and standard deviation were calculated for all baseline characteristics by treatment arm. All time to event outcomes were calculated in days by subtracting the date of randomization from either: (1) the date of event or death; or (2) the trial termination date for those patients not experiencing the defined event. As pre-specified, the primary efficacy analysis was based on the intention-to-treat principle. The intention-to-treat analysis included all randomized subjects and all events during the time from randomization to the trial termination. Trial termination date was fixed as May 31, 2012. A secondary pre-specified on-treatment analysis was also performed, based on patients who were both tolerant and compliant to therapy beyond the first month of randomization. All events during the time from randomization until non-compliance with colchicine treatment regimen were included in this analysis.

The time-to-first-event for all outcomes is presented using a Kaplan-Meier plot. The primary efficacy outcome was analyzed using a cox proportional hazards model including treatment group coded as control or colchicine. The secondary outcomes were analysed similarly. In addition, the primary analysis was stratified by gender, age, diagnosis of diabetes, past myocardial infarction, unstable angina, coronary bypass surgery, coronary angioplasty, and therapy with aspirin, clopidogrel or both, high dose statin therapy (defined as a dose of statin equivalent to atorvastatin of 40 mg or more), beta blockers, calcium blockers and ACE inhibitors.

Results:

Between August 2008 and May 2010, 901 patients with stable coronary disease attending for routine out-patient cardiology review were assessed for eligibility for the study. Of these, 297 (33%) did not meet the entry criteria, 72 (8%) declined to participate and 532 (59%) were enrolled into the study, 250 of whom were randomized to the control group and 282 to treatment. Of those randomized to treatment 32 (11%) reported early intolerance, due to gastrointestinal side effects, and 7 patients subsequently reported that they chose not start therapy. All 532 randomized patients were followed for the duration of the study period which ranged from a minimum of 24 to a maximum of 44 months. Median follow up was 36 months.

Outcomes:

A primary outcome occurred in 55/532 patients, including 15/282 (5.3%) patients assigned to colchicine treatment, and 40/250 (16%) patients assigned to the control group [hazard ratio 0.33, 95% CI; 0.18-0.59; p<0.001, number needed to treat 11). A sensitivity analysis was performed for the primary outcome, adjusting for the usage of calcium channel blockers and beta blocker therapy. These results were consistent with the primary analysis.

The effect of colchicine on the primary outcome was evident early and the benefits of colchicine continued to accrue throughout the follow up period. There was no evidence of differential treatment effects based on any of the clinical or therapeutic variables.

The reduction in the primary outcome was largely driven by the reduction in the number of patients presenting with an ACS, (13/282 (4.6%) vs. 34/250 (13.4%), hazard ratio 0.33; 95% CI; 0.18-0.63; p<0.001). Out of hospital cardiac arrest and non-cardio-embolic ischemic stroke were infrequent but were also reduced in the treatment group.

Of the 47 patients who presented with an ACS, the event was stent related in 8 (17%) (2 in each group had evidence of acute stent thrombosis and 2 in each group had evidence of significant in-stent stenosis). Further analysis confirmed that patients randomized to treatment were less likely to present with an ACS unrelated to stent disease (9/282 (3.2%) vs. 30/250 (12%) hazard ratio 0.26, 95% CI; 0.12-0.55; p<0.001), be it associated with an AMI (4/282 (1.4%) vs. 14/250 (5.6%) hazard ratio 0.25, 95% CI; 0.08-0.76; p=0.014) or UA (5/282 (1.8%) vs. 16/250 (6.4%) hazard ratio 0.27, 95% CI; 0.10-0.75; p=0.011).

Of 39 patients randomized to treatment who did not receive therapy beyond the first month due to early intolerance or non-compliance, 4 (10%) presented with an ACS due to acute stent thrombosis (n=1) and UA (n=3). Patients who were both compliant and tolerant to therapy beyond the first month of randomization had significantly fewer events than the control patients (11/243 (4.5%) vs. 40/250 (16%) hazard ratio 0.29, 95% CI; 0.15-0.56; p<0.001). The results of all on-treatment analyses were consistent with those based upon the intention to treat analyses.

Ten patients in the control group died compared with 4 patients in the colchicine group. Of the 10 controls, 5 died of presumed cardiac cause; 2 following an out-of-hospital cardiac arrest, 2 from cardiogenic shock following myocardial infarction, and 1 following bypass surgery. All 4 patients in the colchicine group died of non-cardiac causes.

The table below shows primary outcome (i.e., cardiovascular event such as acute coronary syndrome, out-of-hospital cardiac arrest or noncardioembolic ischemic stroke) in patients receiving at least one antithrombotic agent, such as aspirin, clopidogrel or warfarin. Most patients also received additional medical such as beta blockers, statins, etc. As seen in the data, a primary outcome was less in patients receiving colchicine and at least one antithrombotic agent (4.5%) than in patients receiving at least one antithrombotic agent but not colchicine (16%). Moreover, primary outcome was less in patients receiving colchicine and at least aspirin (4.67%) than in patients receiving at least aspirin but no colchicine (14.7%). In other words, the addition of colchicine to patients receiving at least one antithrombotic agent, such as aspirin, further reduces the incidence of a primary outcome such as acute coronary syndrome, fatal or non-fatal out of hospital cardiac arrest or non-cardio-embolic ischemic stroke.

|  | Colchicine group | Primary Outcome | Control group | Primary Outcome |
|---|---|---|---|---|
| Total* | 243 | 11 (4.5%) | 250 | 40 (16%) |
| Treated with at least one antithrombotic drugs (at least aspirin, clopidogrel or warfarin or combinations thereof) | 242 | 11 (4.5%) | 250 | 40 (16%) |
| Treated with a least one antiplatelet drug (at least aspirin, clopidogrel or combinations thereof) | 226 | 11 (4.9%) | 236 | 37 (15.6%) |
| Treated with at least aspirin | 214 | 10 (4.67%) | 224 | 33 (14.7%) |
| Treated with Aspirin alone | 173 | 7 (4%) | 197 | 27 (13.7%) |
| Treated with Aspirin + clopidogrel | 33 | 3 (9%) | 25 | 6 (24%) |
| Treated with Aspirin + warfarin | 6 | 0 (0%) | 2 | 0 (0%) |
| Treated with Aspirin + clopidogrel + warfarin | 2 | 0 (0%) |  |  |
| Treated with Clopidogrel alone or warfarin alone (no aspirin) | 28 | 1 (3.45%) | 26 | 7 (26.9%) |
| Treated with Clopidogrel alone | 12 | 1 (8.3%) | 12 | 4 (33%) |
| Treated with Warfarin alone | 16 | 0 (0%) | 14 | 3 (21.4%) |
| No treatment | 1 | 0 (0%) | 0 | n/a |

This trial demonstrates that the addition of colchicine 0.5 mg/day to standard therapy in patients with stable coronary disease significantly reduces the risk of a cardiovascular event, including an ACS, out of hospital cardiac arrest and non-cardio-embolic ischemic stroke. The benefits of colchicine were achieved on a background of widespread use of effective secondary prevention strategies, including high dose statins, as evidenced by the low event rate in the control group. The effect of adding colchicine became evident early, continued to accrue over time and was largely driven by a reduction in ACS unrelated to stent disease.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method of treating and/or reducing the risk of a cardiovascular event in a subject, the method comprising:
   administering colchicine, a salt thereof, and/or any combination thereof to a subject at risk of a cardiovascular event or who has had a cardiovascular event;
   wherein the cardiovascular event is acute coronary syndrome, out-of-hospital cardiac arrest, or noncardioembolic ischemic stroke.

2. The method of claim 1, wherein the composition is administered once per day.

3. The method claim 1, wherein about 0.5 to about 0.75 mg of colchicine, a salt thereof, and/or any combination thereof is administered to the subject.

4. The method of claim 3, wherein about 0.5 to 0.6 mg of colchicine, a salt thereof, and/or any combination thereof is administered to the subject.

5. The method of claim 3, wherein about 0.6 mg of colchicine, a salt thereof, and/or any combination thereof is administered to the subject.

6. The method of claim 1, wherein the composition is administered orally, topically, parenterally, ophthalmically, intraventricularly, intracranially, intraperitoneally, buccally, rectally, vaginally, intranasally, or by aerosol administration and/or inhalation spray.

7. The method of claim 1, wherein the composition is administered in the form of a tablet, capsule, liquid dose, gel, or powder.

8. The method of claim 1, wherein the subject receives concurrent treatment with at least one anticoagulant agent or antithrombotic agent.

9. The method claim 8, wherein the anticoagulant agent is one or more of novel oral anticoagulants (NOACs), coumarins or vitamin K antagonists, heparin, low molecular weight heparin, a synthetic pentasaccharide inhibitor of factor Xa, a factor Xa inhibitor, a thrombin inhibitor, and an antithrombin protein therapeutic.

10. The method of claim 9, wherein:
   (a) the NOAC is dabigatran, rivaroxaban, apixaban, or a combination thereof;
   (b) wherein the coumarin or vitamin K antagonist is one or more of warfarin, acenocoumarol, phenprocoumon, atromentin, brodifacoum, and phenindione;
   (c) wherein the factor Xa inhibitor is one or more of rivaroxaban, apixaban, edoxaban, and darexaban; and/or
   (d) wherein the thrombin inhibitor is one or more of hirudin, lepirudin, bivalirudin, and ximelagatrain.

11. The method of claim 8, wherein the antithrombotic agent is an antiplatelet agent or a thrombolytic agent.

12. The method of claim 11, wherein the antiplatelet agent, the anticoagulant agent, and/or the thrombolytic agent is aspirin.

13. The method of claim 11, wherein the antiplatelet agent is one or more of an irreversible cyclooxygenase inhibitor, an adenosine diphosphate (ADP) receptor inhibitor, a phosphodiesterase inhibitor, a protease-activated receptor-1

(PAR-1) antagonist, a glycoprotein inhibitor, an adenosine reuptake inhibitor, and a thromboxane inhibitor.

14. The method of claim 13, wherein:
   (a) the irreversible cyclooxygenase inhibitor is aspirin and/or triflusal;
   (b) the ADP receptor inhibitor is clopidogrel, prasugrel, ticagrelor, ticlopidine, or a combination thereof;
   (c) the phosphodiesterase inhibitor is cilostazol;
   (d) the PAR-1 antagonist is vorapaxar;
   (e) the glycoprotein inhibitor is abciximab, eptifibatide, tirofiban, or a combination thereof;
   (f) the adenosine reuptake inhibitor is dipyridamole; and/or
   (g) the thromboxane inhibitor is terutroban.

15. The method of claim 11, wherein the thrombolytic agent is tissue plasminogen activator (t-PA).

16. The method of claim 15, wherein the t-PA is alteplase, reteplase, tenecteplase, anistreplase, streptokinase, urokinase, or a combination thereof.

17. The method of claim 1, further comprising co-administering to the subject a therapeutically effective amount of a second agent for the treatment and/or reduction of risk of the cardiovascular event.

18. The method of claim 17, wherein the second agent is a statin.

19. The method of claim 18, wherein the statin is atorvastatin, fluvastatin, lovastatin, pitavastatin, rosuvastatin, simvastatin, pravastatin, any salt thereof, or any combination thereof.

20. The method of claim 1, wherein the subject exhibits the symptoms of or is diagnosed with a coronary disease.

21. The method of claim 20, wherein the coronary disease is a clinically stable coronary disease.

22. The method of claim 1, wherein the subject has the symptoms of or is diagnosed with atherosclerotic vascular disease.

23. The method of claim 22, wherein the subject is concurrently administered an agent for the treatment and/or reduction of the risk of an atherosclerotic vascular disease.

24. The method of claim 23, wherein the atherosclerotic vascular disease is a coronary disease.

25. The method of claim 24, wherein the coronary disease is a clinically stable coronary disease.

26. The method of claim 23, wherein the agent is a statin.

27. The method of claim 26, wherein the statin is atorvastatin, fluvastatin, lovastatin, pitavastatin, rosuvastatin, simvastatin, pravastatin, a salt thereof, or any combination thereof.

28. The method of claim 1, wherein the composition of colchicine is administered as an immediate release formulation.

29. The method of claim 1, wherein the composition is administered for at least two years.

30. A method of treating and/or reducing the risk of acute coronary syndrome, out-of-hospital cardiac arrest, and/or noncardioembolic ischemic stroke in a human subject administered at least one of an antiplatelet agent, an anticoagulant agent, and an thrombolytic agent, the method comprising administering about 0.5 mg to about 0.75 mg of colchicine, a salt thereof, and/or any combination thereof to the subject.

31. A method of treating and/or reducing the risk of a cardiovascular event, which comprises administering about 0.5 mg to about 0.75 mg of colchicine, a salt thereof, and/or any combination thereof to a human subject,
   wherein the human subject is concurrently administered an antiplatelet agent, an anticoagulant agent, a thrombolytic agent, or any combination thereof;
   wherein the cardiovascular event is acute coronary syndrome, cardiac arrest, or noncardio-embolic ischemic stroke;
   wherein acute coronary syndrome is acute myocardial infarction or unstable angina;
   wherein cardiac arrest is associated with asystole, ventricular tachycardia, or ventricular fibrillation; and
   wherein noncardio-embolic ischemic stroke is not attributable to atrial fibrillation or intracranial hemorrhage.

\* \* \* \* \*